United States Patent [19]

Cauwet-Martin et al.

[11] Patent Number: 5,612,025

[45] Date of Patent: Mar. 18, 1997

[54] COSMETIC COMPOSITIONS CONTAINING A SYNERGISTIC MIXTURE OF CONDITIONING POLYMERS

[75] Inventors: Daniele Cauwet-Martin, Paris; Claude Dubief, Le Chesnay, both of France

[73] Assignee: L'Oreal, Paris, France

[21] Appl. No.: 401,887

[22] Filed: Mar. 10, 1995

[30] Foreign Application Priority Data

Mar. 15, 1994 [FR] France .................................. 94 02991

[51] Int. Cl.$^6$ ........................................................ A61K 7/06
[52] U.S. Cl. ........................................ 424/70.17; 424/70.11; 424/70.12
[58] Field of Search .................................. 424/401, 70.11, 424/70.17, 70.12

[56] References Cited

U.S. PATENT DOCUMENTS

| | | | |
|---|---|---|---|
| 2,528,378 | 10/1950 | Mannheimer . | |
| 2,781,354 | 2/1957 | Mannheimer . | |
| 4,157,388 | 6/1979 | Christiansen . | |
| 4,349,532 | 9/1982 | Vanlerberghe et al. | 424/47 |
| 4,390,689 | 6/1983 | Jacquet et al. . | |
| 4,702,906 | 10/1987 | Jacquet et al. . | |
| 4,719,282 | 1/1988 | Nadolsky et al. . | |
| 4,764,365 | 8/1988 | Boothe et al. | 514/772.6 |
| 4,772,462 | 9/1988 | Boothe et al. | 424/70.16 |
| 4,867,966 | 9/1989 | Grollier et al. . | |
| 4,996,059 | 2/1991 | Grollier et al. . | |
| 5,089,252 | 2/1992 | Grollier et al. . | |
| 5,114,428 | 5/1992 | Hoeffkes et al. | 8/405 |
| 5,132,107 | 7/1992 | Lange | 514/345 |
| 5,275,755 | 1/1994 | Sebag et al. | 252/174.15 |
| 5,449,475 | 9/1995 | Cauwet et al. | 252/174.23 |

FOREIGN PATENT DOCUMENTS

| | | |
|---|---|---|
| 0269243 | 6/1983 | European Pat. Off. . |
| 0308190 | 3/1989 | European Pat. Off. . |
| 2470596 | 6/1981 | France . |
| 2519863 | 7/1983 | France . |
| 2680682 | 3/1993 | France . |
| 3731477 | 3/1988 | Germany . |
| 0521748 | 1/1993 | Germany . |
| 2188948 | 10/1987 | United Kingdom . |

*Primary Examiner*—Melvyn I. Marquis
*Assistant Examiner*—Robert H. Harrison
*Attorney, Agent, or Firm*—Finnegan, Henderson, Farabow, Garrett & Dunner, L.L.P.

[57] ABSTRACT

The invention relates to new cosmetic compositions based on a synergistic mixture of conditioning polymers chosen from at least one quaternary polyammonium polymer (a) consisting of a sequence of units corresponding to the following formula (I):

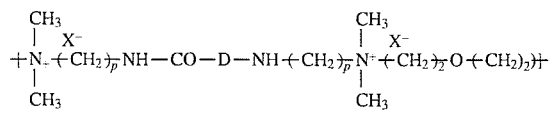

in which p is an integer ranging from 1 to 6, D may not exist or can represent a —(CH$_2$)$_r$—CO— group in which r denotes a number equal to 4 or to 7, X$^-$ is an anion derived from an inorganic or organic acid, where the molecular mass of the polymer (a) is less than 100,000 and at least one polymer (b) consisting of 70% to 90% by weight of diallyldialkylammonium units in which the alkyl radical contains from 1 to 18 carbon atoms and of 30% to 10% by weight of acrylic or methacrylic units, and to their use for washing or for caring for the hair and/or the skin.

27 Claims, No Drawings

COSMETIC COMPOSITIONS CONTAINING A SYNERGISTIC MIXTURE OF CONDITIONING POLYMERS

The subject of the invention is cosmetic compositions for the hair and the skin containing conditioning polymers in specific proportions which produce a synergistic effect.

The use has already been recommended of conditioning polymers, especially cationic polymers, in compositions for washing or caring for the hair, in order to facilitate disentangling of the hair and to give it softness and suppleness. However, the use of cationic polymers for this purpose has various disadvantages. Due to their high affinity for the hair, significant amounts of some of these polymers are deposited during repeated uses and lead to undesirable effects such as an unpleasant feel, stiffening of the hair and an interfibre adhesion which affects the styling. These disadvantages are accentuated in the case of fine hair, which lacks hold, liveliness and body.

Mention may be made of the following documents which describe the use of cationic polymers as cosmetic agents: U.S. Pat. Nos. 4,157,388, 4,390,689, 4,702,906 and 4,719,282, the disclosures of which are hereby incorporated by reference. These patents describe the use of quaternized polymers. The use of these quaternized polymers as sole cosmetic treatment agents is not, however, entirely satisfactory with respect to the hold of the hair.

The use of amphoteric polymers, such as those described in Patent Application EP-A-269,243, the disclosure of which is hereby incorporated by reference, has also been recommended for improving the conditioning properties of hair products. However, the compositions containing only these polymers do not make it possible to obtain satisfactory softness and disentangling.

Moreover, in French Patent Applications FR-A-2,470,596 and FR-A-2,519,863, the disclosures of which are hereby incorporated by reference, cosmetic compositions are provided for the treatment of hair containing a combination of a cationic polymer and an amphoteric polymer. While these compositions are better than the compositions containing only a cationic polymer or only an amphoteric polymer, they are not, however, entirely satisfactory as regards the disentangling and softness properties conferred on the hair.

The inventors have now discovered that the combination of certain conditioning polymers described in the prior documents which have just been mentioned, when they are suitably selected and used in respective proportions varying within well-determined limits, makes it possible, due to a synergistic cosmetic effect, to overcome these disadvantages. This combination, in fact, brings about cosmetic properties which are markedly improved with respect to the properties obtained with one or other of the constituents used alone and with respect to the combinations of the two constituents used in ratios outside the scope of the invention.

In particular, it has been discovered that the compositions obtained according to the invention bring about an improvement in the disentangling (especially on wet hair) and an improvement in the softness of the hair. In addition, the hair is not made lank after repeated applications. Moreover, the compositions of the invention, applied to the skin especially in the form of a foam bath or of a shower gel, bring about an improvement in the softness of the skin.

The subject of the invention is therefore a cosmetic composition which comprises:

at least one quaternary polyammonium polymer (a) consisting of a sequence of units corresponding to the following formula (I):

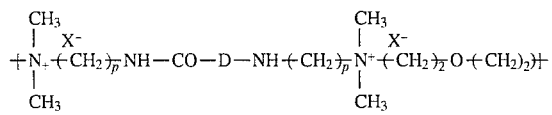

in which:
p is an integer ranging from 1 to 6 whose value in each instance can be the same or different, D may not exist or is a $(CH_2)_r$—CO— group in which r denotes a number equal to 4 or to 7, $X^-$ is an anion derived from an inorganic or organic acid, where the molecular mass of the polymer (a) is less than 100,000 and preferably less than or equal to 50,000, and at least one polymer (b) consisting of 70 to 90% by weight of diallyldialkyl-ammonium units in which the alkyl radicals, which can be the same or different, contain from 1 to 18 carbon atoms and of 30% to 10% by weight of acrylic or methacrylic units, where polymers (a) and (b) are present in a proportion sufficient to produce a synergistic cosmetic activity.

The use is preferred, among the above polymers (a), of:
i) polymers in which D represents a —$(CH_2)_4$—CO— group and X denotes a chlorine atom; a polymer of this type is sold by the company Miranol under the name of MIRAPOL-AD1, ii) polymers in which D represents a —$(CH_2)_7$—CO— group and X denotes a chlorine atom; a polymer of this type is sold by the company Miranol under the name of MIRAPOL-AZ1, iii) polymers in which D does not exist and X denotes a chlorine atom; a polymer of this type is sold by the company Miranol under the name of MIRANOL-A15, iiii) block copolymers formed from units corresponding to the polymers described in paragraphs i) and iii) above and sold by the company Miranol under the names of MIRAPOL-9, MIRAPOL-175 and MIRAPOL-95.

Such polymers can be prepared according to the processes described in U.S. Pat. Nos. 4,157,388, 4,390,689, 4,702,906 and 4,719,282, the disclosures of which are hereby incorporated by reference.

Preference is given, among the polymers (b), to copolymers of diallyldimethylammonium or diallyl-diethylammonium chloride and of acrylic acid with a molecular weight ranging from 50,000 to 10,000,000 and preferably from 200,000 to 5,000,000. A polymer of this type, and particularly preferred according to the invention, is the copolymer of diallyldimethylammonium chloride and of acrylic acid (80/20 by weight) sold as a solution containing 35% of active material by the companies Calgon Corp and Merck under the name of MERQUAT 280.

The synergistic effect between the polymers (a) and (b) defined above generally appears in an (a)/(b) weight ratio from 0.1:1 to 3:1. However, the exact range of the suitable weight ratios (i.e., for which the synergistic effect is effectively obtained) can vary depending on the nature of the polymer (a) used. Thus, by way of example, a noteworthy synergistic effect on the cosmetic properties could be observed in the following specific cases:

a combination between a polymer (a) as defined in paragraph iii) above and a polymer (b), for a range of (a)/(b) weight ratios from 0.1:1 to 1.5:1, a combination between a polymer (a) as defined in paragraph i) above and a polymer (b) or between a polymer (a) as defined in paragraph ii) above and a polymer (b), for a range of (a)/(b) weight ratios from 1.25:1 to 1.75:1, a combination between a polymer (a) as defined in paragraph iii) above and a polymer (b), for a range of (a)/(b) weight ratios from 0.5:1 to 3:1.

In the compositions according to the invention, the amount by weight of the polymer (a) is preferably from 0.05% to 4% and more preferably from 0.1% to 3%. The amount by weight of the polymer (b) is preferably from 0.1% to 8% and more preferably from 0.2% to 6%, with respect to the total weight of the composition.

The compositions of the invention additionally advantageously contain at least one surface-active agent which is generally present in an amount ranging from 0.1% to 40% by weight, preferably from 3% to 40% and more preferably from 5% to 30%, with respect to the total weight of the composition.

This surface-active agent can be chosen from anionic, amphoteric, zwitterionic, non-ionic or cationic surface-active agents or their mixtures. Mention may be made, among anionic surface-active agents, of the salts (in particular alkali metal, especially sodium, salts, ammonium salts, amine salts, aminoalcohol salts or magnesium salts) of the following compounds: alkyl ether sulphates, alkylamido ether sulphates, alkylaryl polyether sulphates, monglyceride sulphates; alkyl sulphonates, alkyl sulphates, alkyl phosphates, alkylamide sulphonates, alkylaryl sulphonates, α-olefin sulphonates, paraffin sulphonates; alkyl sulphosuccinates, alkyl ether sulphosuccinates, alkylamide sulphosuccinates; alkyl sulphosuccinamates; alkyl sulphoacetates; alkyl ether phosphates; acyl sarcosinates and N-acyl taurates. The alkyl or acyl radical of these various compounds preferably contains from 12 to 20 carbon atoms.

Mention may alternatively be made, among anionic surface-active agents, of the salts of fatty acids such as the salts of oleic, ricinoleic, palmitic and stearic acids, coconut oil acid or hydrogenated coconut oil acid, or acyl lactylates in which the acyl radical contains 8 to 20 carbon atoms. It is also possible to use weakly anionic surface-active agents, such as alkyl D-galactosiduronic acids and their salts, as well as polyoxyalkylenated ether carboxylic acids, in particular those containing from 2 to 24 ethylene oxide groups, and their mixtures. The anionic surface-active agents of polyoxyalkylenated ether carboxylic acid type are, in particular, those which correspond to the following formula (II):

$$R_1\text{---}(OC_3H_6)_x\text{---}(OC_2H_4)_y\text{---}OCH_2COOA \qquad (II)$$

in which:

$R_1$ denotes a linear or branched $C_8$–$C_{22}$ alkyl or alkenyl group, a ($C_8$–$C_9$)alkylphenyl group, or a group R'—CONH—CH$_2$— in which R' denotes a $C_{11}$—$C_{21}$ alkyl or alkenyl radical, x is an integer or decimal number which can vary from 0 to 6, and y is an integer or decimal number which can vary from 2 to 24 and preferably from 3 to 10, A denotes H, ammonium, Na, K, Li, Mg or a monoethanolamine or triethanolamine residue. It is also possible to use mixtures of compounds of formula (II), in particular mixtures in which the $R_1$ groups are different.

Compounds of formula (II) are sold, for example, by the Company Chem Y under the names AKYPOS (NP40, NP70, OP40, OP80, RLM25, RLM38, RLMQ 38 NV, RLM 45, RLM 45 NV, RLM 100, RLM 100 NV, RO 20, RO 90, RCS 60, RS 60, RS 100 or RO 50) or by the Company Sandoz under the names SANDOPAN (DTC Acid or DTC).

According to a preferred embodiment of the invention, use is made, as anionic surface-active agent, of at least one compound of the carboxylic acid type of formula (II) indicated above, in which $R_1$ denotes a ($C_{12}$–$C_{14}$)alkyl, oleyl, cetyl or stearyl radical, A denotes a hydrogen or sodium atom, x=0 and y ranges from 3 to 10. Use is made, for example, of the commercial product sold by the Company Chem Y under the name RLM 45 ($R_1$=($C_{12}$–$C_{14}$)alkyl; mean value of y=4.5; x=0 and A=H).

The non-ionic surface-active agents can be chosen from polyethoxylated, polypropoxylated or polyglycerolated alcohols, α-diols, alkylphenols or fatty acids having a fatty chain containing, for example, 8 to 18 carbon atoms, it being possible for the number of ethylene oxide or propylene oxide groups to range especially from 2 to 50 and it being possible for the number of glycerol groups to range especially from 2 to 30. Mention may also be made of copolymers of ethylene oxide and of propylene oxide or of condensates of ethylene oxide and of propylene oxide with fatty alcohols; of polyethoxylated fatty amides preferably having from 2 to 30 mol of ethylene oxide or of polyglycerolated fatty amides containing, on average, 1 to 5 glycerol groups and in particular 1.5 to 4; polyethoxylated fatty amines preferably having 2 to 30 mol of ethylene oxide; oxyethylenated fatty acid esters of sorbitan having from 2 to 30 mol of ethylene oxide; fatty acid esters of sucrose, fatty acid esters of polyethylene glycol, alkyl polyglycosides, derivatives of N-alkylglucamine, or amine oxides such as ($C_{10}$–$C_{14}$)alkylamine oxides or N-acylaminopropyl-morpholine oxides. Alkyl polyglycosides and polyglycerols are among the most particularly preferred non-ionic surface-active agents.

The amphoteric or zwitterionic surface-active agents are preferably derivatives of secondary or tertiary aliphatic amines, in which the aliphatic radical is a linear or branched chain containing 8 to 18 carbon atoms and containing at least one water-solubilizing anionic group (for example, carboxylate, sulphonate, sulphate, phosphate or phosphonate). Mention may further be made of alkyl ($C_8$–$C_{20}$) betaines, sulphobetaines, alkyl ($C_8$–$C_{20}$) amidoalkyl ($C_1$–$C_6$) betaines or alkyl ($C_8$–$C_{20}$) amidoalkyl ($C_1$–$C_6$) sulphobetaines.

Mention may be made, among the amine derivatives, of the products sold under the name MIRANOL, as described in U.S. Pat. No. 2,528,378 and U.S. Pat. No. 2,781,354, the disclosures of which are hereby incorporated by reference, and referenced in the CTFA dictionary, 3rd edition, 1982, under the names of Amphocarboxyglicinates and Amphocarboxypropionates, of respective formulae:

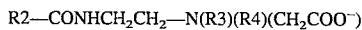

$$R2\text{---}CONHCH_2CH_2\text{---}N(R3)(R4)(CH_2COO^-)$$

in which: R2 denotes an alkyl radical of an acid R2—COOH present in hydrolyzed coconut oil or a heptyl, nonyl or undecyl radical, R3 denotes a β-hydroxyethyl group and R4 denotes a carboxymethyl group; and

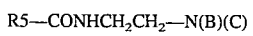

$$R5\text{---}CONHCH_2CH_2\text{---}N(B)(C)$$

in which:

B represents —CH$_2$CH$_2$OX', C represents —(CH$_2$)$_z$—Y', with z=1 or 2,

X' denotes the —CH$_2$CH$_2$—COOH group or a hydrogen atom,

Y' denotes —COOH or the —CH$_2$—CHOH—SO$_3$H radical,

R5 denotes an alkyl radical of an acid R5—COOH present in hydrolyzed coconut oil or in hydrolyzed linseed oil, an alkyl, especially C$_7$, C$_9$, C$_{11}$ or C$_{13}$, radical, a C$_{17}$ alkyl radical and its iso form, or an unsaturated C$_{17}$ radical. Mention may be made, for example, of the cocoamphocarboxyglycinate sold under the trade name concentrated MIRANOL C2M by the company Miranol.

Mention may be made, among cationic surface-active agents, of, in particular: salts of optionally polyoxyalkylenated primary, secondary or tertiary fatty amines; quaternary ammonium salts such as tetraalkylammonium, alkylamidoalkyltrialkylammonium, trialkylbenzylammonium, trialkylhydroxyalkylammonium or alkylpyridinium chlorides or bromides; imidazoline derivatives; or amine oxides with a cationic nature. The concentration of these cationic surface-active agents preferably ranges from 0.1% to 10% by weight with respect to the total weight of the composition.

The anionic surface-active agents are preferably used as a mixture with amphoteric surface-active agents. In this case, the weight ratio of the first to the second can vary from 0.5 to 10 and preferably from 1 to 5.

The compositions in accordance with the invention can additionally contain conventional adjuvants. These are, for example, fragrances, solvents, preserving agents, sequestering agents, thickening agents, emollients, foam-modifying agents, acidifying agents or basifying agents.

The thickening agents can be chosen especially from sodium alginate, gum arabic, cellulose derivatives such as methyl cellulose, hydroxymethyl cellulose, hydroxyethyl cellulose, hydroxypropyl cellulose or hydroxypropylmethyl cellulose, guar gum or its derivatives, xanthan gums, scleroglucans, crosslinked polyacrylic acids, propylene glycol oleate oxyethylenated with 55 mol of ethylene oxide and ethers of fatty alcohols having from 27 to 44 carbon atoms. The thickening agent can also be obtained by mixing polyethylene glycol and polyethylene glycol stearates or distearates or by mixing phosphoric esters and amides.

These thickening agents are preferably used in proportions which can range from 0.5 to 5% by weight with respect to the total weight of the composition. The aqueous medium can contain, in addition to water, cosmetically acceptable solvents such as monoalcohols, polyalcohols, glycol ethers or fatty acid esters, used alone or as a mixture. Mention may more particularly be made, among these solvents, of lower alcohols such as ethanol or isopropanol, polyalcohols such as ethylene glycol, diethylene glycol or propylene glycol, glycol ethers and alkyl ethers of glycol or of diethylene glycol. The solvents are preferably used in proportions of from 0.5 to 10% by weight with respect to the total weight of the composition.

The compositions according to the invention can also contain dyes, viscosity-modifying agents, pearlescence agents, moisturizing agents, anti-dandruff agents, anti-seborrhoeic agents, sunscreens, optionally organomodified, volatile or nonvolatile silicones, or conditioning agents other than those of the invention, such as optionally polymeric cationic compounds, hydrocarbon oils, proteins, vitamins and the like.

The pH of the compositions according to the invention generally ranges from 4 to 8 and preferably from 5 to 7.

The compositions in accordance with the invention can be used for washing and treating the hair and/or the skin. The compositions of the invention can more particularly be provided in the form of a rinsing or non-rinsing conditioner or of permanent wave, hair straightening, dyeing or bleaching compositions or alternatively in the form of rinsing compositions, to be applied before or after a dyeing, a bleaching, a permanent wave or a hair straightening or alternatively between the two stages of a permanent wave or of a hair straightening.

The compositions of the invention can alternatively be provided in the form of washing compositions for the body, and in particular in the form of solutions or gels for the bath or the shower or of make-up removal products. The compositions according to the invention can also be provided in the form of aqueous or aqueous/alcoholic lotions for caring for the skin and the hair.

A person skilled in the art determines, from the various additives listed above, those which are suitable for the desired application.

The examples which follow will illustrate the invention without, however, limiting it.

EXAMPLE 1

Various conditioning lotions were prepared containing:

| | |
|---|---|
| a) a polymer (a) chosen from various products sold under the general name of Mirapol ® by the Company Miranol, namely:<br>MIRAPOL 175<br>MIRAPOL A15<br>MIRAPOL AD1<br>MIRAPOL 9<br>MIRAPOL AZ1<br>at the rate of | x g |
| b) a copolymer (b) of diallyldimethylammonium chloride and of acrylic acid, containing 35% of active material (AM), sold under the name of MERQUAT 280 by the Company Merck, at the rate of | y g |
| c) HCl q.s. | pH 5.5 |
| d) Preserving agents q.s. | |
| e) Water q.s. for | 100 g |

These lotions (numbered below from 1 to 17) had different x/y weight ratios of the polymer (a) to the polymer (b); in addition, comparative lotions were made to correspond to each of these lotions which: either contained only the polymer (a) at the concentration x+y (lotions of type A), or only contained the polymer (b), also at the concentration x+y (lotions of type B).

The exact compositions of all these lotions are given in Table I below (the values are expressed in g):

TABLE I

| Polymers | Lotions | | | | | | | | |
|---|---|---|---|---|---|---|---|---|---|
| | 1 | 1A | 1B | 2 | 2A | 2B | 3 | 3A | 3B |
| (a): MIRAPOL 175 | 0.1 | 1.1 | | 0.5 | 1.5 | | 3 | 4 | |
| (b): MERQUAT 280 | 1 | | 1.1 | 1 | | 1.5 | 1 | | 4 |
| Weight ratio (a)/(b) | 0.1 | | | 0.5 | | | 3 | | |

| Polymers | Lotions | | | | | | | | |
|---|---|---|---|---|---|---|---|---|---|
| | 4 | 4A | 4B | 5 | 5A | 5B | 6 | 6A | 6B |
| (a): MIRAPOL A15 | 0.1 | 1.1 | | 1.5 | 2.5 | | 2 | 3 | |
| (b): MERQUAT 280 | 1 | | 1.1 | 1 | | 2.5 | 1 | | 3 |
| Weight ratio (a)/(b) | 0.1 | | | 1.5 | | | 2 | | |

| Polymers | Lotions | | | | | | | | | | |
|---|---|---|---|---|---|---|---|---|---|---|---|
| | 7 | 7A | 7B | 8 | 8A | 8B | 9 | 9A | 9B | 10 | 10A | 10B |
| (a): MIRAPOL AD1 | 1 | 2 | | 1.25 | 2.25 | | 1.75 | 2.75 | | 2 | 3 | |
| (b): MERQUAT 280 | 1 | | 2 | 1 | | 2.25 | 1 | | 2.75 | 1 | | 3 |
| Weight ratio (a)/(b) | 1 | | | 1.25 | | | 1.75 | | | 2 | | |

| Polymers | Lotions | | | | | | | | |
|---|---|---|---|---|---|---|---|---|---|
| | 11 | 11A | 11B | 12 | 12A | 12B | 13 | 13A | 13B |
| (a): MIRAPOL 9 | 0.5 | 1.5 | | 2 | 3 | | 3 | 4 | |
| (b): MERQUAT 280 | 1 | | 1.5 | 1 | | 3 | 1 | | 4 |
| Weight ratio (a)/(b) | 0.5 | | | 2 | | | 3 | | |

| Polymers | Lotions | | | | | | | | |
|---|---|---|---|---|---|---|---|---|---|
| | 14 | 14A | 14B | 15 | 15A | 15B | 16 | 16A | 16B | 17 | 17A | 17B |
| (a): MIRAPOL AZ1 | 1 | 2 | | 1.25 | 2.25 | | 1.75 | 2.75 | | 2 | 3 | |
| (b): MERQUAT 280 | 1 | | 2 | 1 | | 2.25 | 1 | | 2.75 | 1 | | 3 |
| Weight ratio (a)/(b) | 1 | | | 1.25 | | | 1.75 | | | 2 | | |

The following procedure was then carried out: identical locks each having 2.5 g of permanent-waved hair were respectively treated (at the rate of 1 g of lotion per lock) with each of the lotions in the above table and then rinsed with water after standing for 2 minutes.

The disentangling in the wet state of the hair treated with these lotions was then compared using a sensory evaluation test. The object of the test used is the grading, by a jury consisting of 10 judges, of each series of 3 samples (for example, the series 1, 1A and 1B) as an increasing or decreasing function of the efficiency of the disentangling (ease of passage of the comb). The 3 samples relating to the same series were presented simultaneously to the judge, who was asked to grade them from the easiest to disentangle to the most difficult. Statistical analysis of the results was carried out using the tables of A. Kramer (Food Technology, 17–(12), 124–125, 1963).

The results are recorded in Table II given below.

TABLE II

| LOTIONS | JUDGES | | | | | | | | | | SUM OF THE RANKINGS |
|---|---|---|---|---|---|---|---|---|---|---|---|
| | 1 | 2 | 3 | 4 | 5 | 6 | 7 | 8 | 9 | 10 | |
| 1 | 2 | 2 | 2 | 2 | 2 | 2 | 2 | 2 | 2 | 2 | 20 |
| 1A | 3 | 3 | 3 | 3 | 3 | 3 | 3 | 3 | 3 | 3 | 30 |
| 1B | 1 | 1 | 1 | 1 | 1 | 1 | 1 | 1 | 1 | 1 | 10 |
| 2 | 1 | 1 | 1 | 1 | 1 | 1 | 1 | 1 | 1 | 1 | 10 |
| 2A | 2 | 2 | 2 | 2 | 2 | 2 | 2 | 2 | 2 | 2 | 20 |
| 2B | 3 | 3 | 3 | 3 | 3 | 3 | 3 | 3 | 3 | 3 | 30 |
| 3 | 1 | 2 | 1 | 2 | 1 | 1 | 1 | 1 | 1 | 1 | 12 |
| 3A | 2 | 1 | 2 | 1 | 2 | 2 | 2 | 2 | 2 | 2 | 18 |
| 3B | 3 | 3 | 3 | 3 | 3 | 3 | 3 | 3 | 3 | 3 | 30 |
| 4 | 1 | 1 | 1 | 1 | 1 | 1 | 1 | 1 | 1 | 1 | 10 |

TABLE II-continued

| LOTIONS | \multicolumn{10}{c}{JUDGES} | SUM OF THE RANKINGS |
|---|---|---|---|---|---|---|---|---|---|---|---|
|  | 1 | 2 | 3 | 4 | 5 | 6 | 7 | 8 | 9 | 10 |  |
| 4A | 2 | 2 | 2 | 2 | 2 | 2 | 2 | 2 | 2 | 2 | 20 |
| 4B | 3 | 3 | 3 | 3 | 3 | 3 | 3 | 3 | 3 | 3 | 30 |
| 5 | 1 | 1 | 1 | 1 | 1 | 1 | 1 | 1 | 1 | 1 | 10 |
| 5A | 2 | 2 | 2 | 2 | 2 | 2 | 2 | 2 | 2 | 2 | 20 |
| 5B | 3 | 3 | 3 | 3 | 3 | 3 | 3 | 3 | 3 | 3 | 30 |
| 6 | 2 | 2 | 2 | 2 | 2 | 2 | 2 | 2 | 2 | 2 | 20 |
| 6A | 3 | 3 | 3 | 3 | 3 | 3 | 3 | 3 | 3 | 3 | 30 |
| 6B | 1 | 1 | 1 | 1 | 1 | 1 | 1 | 1 | 1 | 1 | 10 |
| 7 | 2 | 2 | 2 | 2 | 2 | 2 | 2 | 2 | 2 | 2 | 20 |
| 7A | 3 | 3 | 3 | 3 | 3 | 3 | 3 | 3 | 3 | 3 | 30 |
| 7B | 1 | 1 | 1 | 1 | 1 | 1 | 1 | 1 | 1 | 1 | 10 |
| 8 | 1 | 2 | 1 | 2 | 1 | 1 | 1 | 1 | 1 | 1 | 12 |
| 8A | 3 | 3 | 3 | 3 | 3 | 3 | 3 | 3 | 3 | 3 | 30 |
| 8B | 2 | 1 | 2 | 1 | 2 | 2 | 2 | 2 | 2 | 2 | 18 |
| 9 | 1 | 1 | 2 | 2 | 2 | 1 | 1 | 1 | 1 | 1 | 13 |
| 9A | 2 | 2 | 1 | 1 | 1 | 2 | 2 | 2 | 2 | 2 | 17 |
| 9B | 3 | 3 | 3 | 3 | 3 | 3 | 3 | 3 | 3 | 3 | 30 |
| 10 | 2 | 2 | 2 | 2 | 2 | 2 | 2 | 2 | 2 | 2 | 20 |
| 10A | 1 | 1 | 1 | 1 | 1 | 1 | 1 | 1 | 1 | 1 | 10 |
| 10B | 3 | 3 | 3 | 3 | 3 | 3 | 3 | 3 | 3 | 3 | 30 |
| 11 | 1 | 2 | 1 | 1 | 2 | 1 | 1 | 1 | 1 | 1 | 12 |
| 11A | 2 | 1 | 2 | 2 | 1 | 2 | 2 | 2 | 2 | 2 | 18 |
| 11B | 3 | 3 | 3 | 3 | 3 | 3 | 3 | 3 | 3 | 3 | 30 |
| 12 | 1 | 1 | 1 | 1 | 1 | 1 | 1 | 1 | 1 | 1 | 10 |
| 12A | 2 | 2 | 2 | 2 | 2 | 2 | 2 | 2 | 2 | 2 | 20 |
| 12B | 3 | 3 | 3 | 3 | 3 | 3 | 3 | 3 | 3 | 3 | 30 |
| 13 | 1 | 1 | 1 | 1 | 2 | 1 | 2 | 1 | 1 | 1 | 12 |
| 13A | 3 | 3 | 3 | 3 | 3 | 3 | 3 | 3 | 3 | 3 | 30 |
| 13B | 2 | 2 | 2 | 2 | 1 | 2 | 1 | 2 | 2 | 2 | 18 |
| 14 | 2 | 2 | 2 | 2 | 2 | 2 | 2 | 2 | 2 | 2 | 20 |
| 14A | 3 | 3 | 3 | 3 | 3 | 3 | 3 | 3 | 3 | 3 | 30 |
| 14B | 1 | 1 | 1 | 1 | 1 | 1 | 1 | 1 | 1 | 1 | 10 |
| 15 | 1 | 1 | 1 | 1 | 1 | 1 | 1 | 1 | 1 | 1 | 10 |
| 15A | 2 | 2 | 2 | 2 | 2 | 2 | 2 | 2 | 2 | 2 | 20 |
| 15B | 3 | 3 | 3 | 3 | 3 | 3 | 3 | 3 | 3 | 3 | 30 |
| 16 | 1 | 1 | 1 | 1 | 1 | 1 | 1 | 1 | 1 | 1 | 10 |
| 16A | 2 | 2 | 2 | 2 | 2 | 2 | 2 | 2 | 2 | 2 | 20 |
| 16B | 3 | 3 | 3 | 3 | 3 | 3 | 3 | 3 | 3 | 3 | 30 |
| 17 | 2 | 2 | 2 | 2 | 2 | 2 | 2 | 2 | 2 | 2 | 20 |
| 17A | 3 | 3 | 3 | 3 | 3 | 3 | 3 | 3 | 3 | 3 | 30 |
| 17B | 1 | 1 | 1 | 1 | 1 | 1 | 1 | 1 | 1 | 1 | 10 |

The results above clearly show that synergistic effects between the polymers (a) and the polymer (b) appear within the following (a)/(b) weight ratio ranges:

- [0.5–3] in the context of a polymer (a) of the MIRAPOL 175 type (see lotions 1 to 3B) or of the MIRAPOL 9 type (see lotions 11 to 13B)
- [0.1–1.5] in the context of a polymer (a) of the MIRAPOL A15 type (see lotions 4 to 6B)
- [1.25–1.75] in the context of a polymer (a) of the MIRAPOL AD1 type (see lotions 7 to 10B) or of the MIRAPOL AZ1 type (see lotions 14 to 17B).

EXAMPLE 2

An example illustrating a shampoo in accordance with the invention is given here.

| | |
|---|---|
| Triethanolamine lauryl ether sulphate (C12/C14 at 70/30) as a 40% aqueous solution (EMPICOL TL 40/FL from Albright & Wilson) | 15 g AM |
| Poly (n = 6) N-[(dimethylammonio)propyl]-N'-[3-(ethyleneoxyethylenedimethylammonio)propyl]uronium dichloride (MIRAPOL A15 from Rhône-Poulenc) | 1 g AM |
| Copolymer of dimethyldiallylammonium chloride and of acrylic acid (80/20) as a 35% aqueous solution (MERQUAT 280 from Merck) | 1 g AM |
| Preserving agents, fragrances and dyes | q.s. |
| HCl q.s. | pH 5 |
| Water q.s. for | 100 g |

EXAMPLE 3

Another example of a shampoo in accordance with the invention is given here.

| | |
|---|---|
| Alkyl (C9/C10/C11 at 20/40/40% by weight) (1→4)polyglucoside as a 50% aqueous solution (APG 300 from Henkel) | 15 g AM |
| Quaternary polyammonium chloride (MW: 20,000) as a 62% aqueous solution (MIRAPOL 175 from Rhône-Poulenc) | 0.5 g AM |
| Copolymer of dimethyldiallylammonium chloride and of acrylic acid (80/20) as a 35% aqueous solution (MERQUAT 280 from Merck) | 1 g AM |
| Preserving agents, fragrances and dyes | q.s. |
| HCl q.s. | pH 6 |
| Water q.s. for | 100 g |

EXAMPLE 4

An example illustrating a conditioner in accordance with the invention is given here.

| | |
|---|---|
| Cetyltrimethylammonium chloride as a 25% aqueous solution (DEHYQUAT A from Henkel) | 3 g AM |
| Quaternary polyammonium chloride (MW: 50,000) as a 50% aqueous solution (MIRAPOL AZ1 from Rhône-Poulenc) | 2 g AM |
| Copolymer of dimethyldiallylammonium chloride and of acrylic acid (80/20) as a 35% aqueous solution (MERQUAT 280 from Merck) | 1.33 g AM |
| Hydroxyethyl cellulose (NATROSOL 250 HHR from Aqualon) | 2.5 g |
| Mixture of cetylstearyl alcohol and cetylstearyl alcohol oxyethylenated with 33 mol of EO (80/20) (DESHCONET 390 from Tensia) | 2 g |
| NaOH q.s. | pH 7 |
| Water q.s. for | 100 g |

EXAMPLE 5

Another example of a conditioner in accordance with the invention is given here.

| | |
|---|---|
| Behenyltrimethylammonium chloride at 80% in a water/isopropanol mixture (GENAMIN KDM-F from Hoechst) | 2.5 g AM |
| Quaternary polyammonium chloride (MW: 50,000) as a 60% aqueous solution (MIRAPOL AD1 from Rhône-Poulenc) | 1.5 g AM |
| Copolymer of dimethyldiallylammonium chloride and of acrylic acid (80/20) as a 35% aqueous solution (MERQUAT 280 from Merck) | 1 g AM |
| Mixture of cetylstearyl alcohol and cetylstearyl alcohol oxyethylenated with 33 mol of EO (80/20) (DESHCONET 390 from Tensia) | 3 g |
| HCl q.s. | pH 4.5 |
| Water q.s. for | 100 g |

EXAMPLE 6

An example illustrating a shower gel in accordance with the invention is given here.

| | |
|---|---|
| Lauryl (C12/C14 at 70/30) ether carboxylic acid containing 4.5 mol of ethylene oxide, as a 90% aqueous solution (AKYPO RLM 45 from Lambert Rivière) | 15 g AM |
| Sodium lauryl ether sulphate (C12/C14 at 70/30) containing 2 mol of ethylene oxide, as a 28% aqueous solution (EMPICOL ESB/3FL from Albright & Wilson) | 10 g AM |
| Quaternary polyammonium chloride (MW: 20,000) as a 62% aqueous solution (MIRAPOL 9 from Rhône-Poulenc) | 0.8 g AM |
| Copolymer of dimethyldiallylammonium chloride and of acrylic acid (80/20) as a 35% aqueous solution (MERQUAT 280 from Merck) | 1.2 g AM |
| Pure glycerol | 1.5 g |
| Preserving agents, fragrances q.s. | |
| NaOH q.s. | pH 7.5 |
| Water q.s. for | 100 g |

What is claimed is:

1. A cosmetic composition comprising:

at least one quaternary polyammonium polymer (a) consisting essentially of a sequence of units corresponding to the following formula (I):

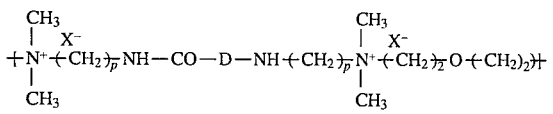

in which p is an integer ranging from 1 to 6 whose value in each instance can be the same or different, D may not exist or is a $-(CH_2)_r-CO-$ group in which r is a number equal to 4 or to 7, $X^-$ is an anion derived from an inorganic or organic acid, at least one polymer (b) consisting essentially of 70% to 90% by weight of diallyldialkylammonium units in which the alkyl radicals, which can be the same or different, contain from 1 to 18 carbon atoms, and 30% to 10% by weight of acrylic or methacrylic units, wherein said polymers (a) and (b) are present in a proportion sufficient to produce a synergistic cosmetic activity.

2. A composition according to claim 1, wherein the polymer (a) is a polymer in which D does not exist and X represents a chlorine atom.

3. A composition according to claim 1, wherein the polymer (a) is a polymer in which D represents a $-(CH_2)_4-CO-$ group and X represents a chlorine atom.

4. A composition according to claim 1, wherein the polymer (a) is a polymer in which D represents a $-(CH_2)_7-CO-$ group and X represents a chlorine atom.

5. A composition according to claim 1, wherein the polymer (a) is a block copolymer formed from (i) a polymer in which D does not exist and X represents a chlorine atom or (ii) a polymer in which D represents a $-(CH_2)_4-CO-$ group and X represents a chlorine atom.

6. A composition according to claim 1, wherein the weight ratio of polymer (a)/polymer (b) ranges from 0.1:1 to 3:1.

7. A composition according to claim 2, wherein the weight ratio of polymer (a)/polymer (b) ranges from 0.1:1 to 1.5:1.

8. A composition according to claim 3, wherein the weight ratio of polymer (a)/polymer (b) ranges from 1.25:1 to 1.75:1.

9. A composition according to claim 4, wherein the weight ratio of polymer (a)/polymer (b) ranges from 1.25:1 to 1.75:1.

10. A composition according to claim 5, wherein the weight ratio of polymer (a)/polymer (b) ranges from 0.5:1 to 3:1.

11. A composition according to claim 1, wherein the polymer (b) is a copolymer of diallyldimethylammonium or diallyldiethylammonium chloride and of acrylic acid.

12. A composition according to claim 1, wherein the polymer (a) is present in an amount of 0.05% to 4% by weight with respect to the total weight of the composition.

13. A composition according to claim 12, wherein the polymer (a) is present in an amount of 0.1% to 3% by weight with respect to the total weight of the composition.

14. A composition according to claim 1, wherein the polymer (b) is present in an amount of 0.1% to 8% by weight with respect to the total weight of the composition.

15. A composition according to claim 14, wherein the polymer (b) is present in an amount of 0.2% to 6% by weight with respect to the total weight of the composition.

16. A composition according to claim 1, wherein said composition has a pH from 4 to 8.

17. A composition according to claim 16, wherein said composition has a pH from 5 to 7.

18. A composition according to claim 1, further comprising at least one surface-active agent, said at least one surface-active agent being an anionic, cationic, non-ionic, amphoteric or zwitterionic surface-active agent.

19. A composition according to claim 18, wherein said at least one surface-active agent is present at a concentration from 0.1% to 40% by weight with respect to the total weight of the composition.

20. A composition according to claim 19, wherein said at least one surface-active agent is present at a concentration from 3% to 40% by weight with respect to the total weight of the composition.

21. A composition according to claim 20, wherein said at least one surface-active agent is present at a concentration from 5% to 30% by weight with respect to the total weight of the composition.

22. A composition according to claim 1, further comprising at least one additive, said additive being a fragrance, solvent, preserving agent, sequestering agent, thickening agent, emollient, foam-modifying agent, acidifying or basifying agent, dye, viscosity-modifying agent, pearlescence agent, moisturizing agent, anti-dandruff agent, anti-seborrhoeic agent, sunscreen, (nano)pigment, non-organomodified volatile or nonvolatile silicone, organomodified volatile or nonvolatile silicone, or conditioning agent other than the polymers (a) and (b).

23. A composition according to claim 22, said other conditioning agent being a polymeric or non-polymeric cationic compound, hydrocarbon oil, or protein.

24. A composition according to claim 1, wherein said composition is provided in the form of a shampoo, a rinsing conditioner, a composition for permanent-waving, straightening, dyeing or bleaching the hair, a rinsing composition, a washing composition for the body, or a lotion.

25. A method for washing or for caring for the hair and/or for the skin comprising the step of contacting said hair or said skin with a composition as defined in claim 1.

26. A cosmetic composition comprising:

at least one quaternary polyammonium polymer (a) consisting of a sequence of units corresponding to the following formula (I):

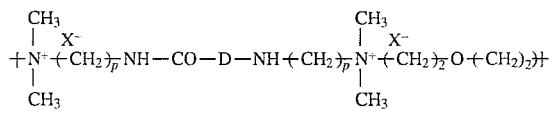

in which p is an integer ranging from 1 to 6,

D may not exist or is a —$(CH_2)_r$—CO— group in which r is a number equal to 4 or to 7, $X^-$ is an anion derived from an inorganic or organic acid, at least one polymer (b) consisting of 70% to 90% by weight of diallyldialkylammonium units in which the alkyl radical contains from 1 to 18 carbon atoms, and 30% to 10% by weight of acrylic or methacrylic units, wherein said polymers (a) and (b) are present in a proportion sufficient to produce a synergistic cosmetic activity.

27. A cosmetic composition comprising:

at least one quaternary polyammonium polymer (a) consisting essentially of a sequence of units corresponding to the following formula (I):

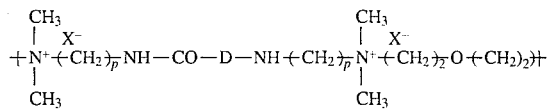

in which p is independently an integer ranging from 1 to 6,

D may not exist or is a —$(CH_2)_r$—CO— group in which r is a number equal to 4 or to 7, $X^-$ is an anion derived from an inorganic or organic acid, at least one polymer (b) consisting essentially of diallyldialkylammonium units in which the alkyl radical contains from 1 to 18 carbon atoms, and acrylic or methacrylic units, wherein said polymers (a) and (b) are present in a proportion sufficient to produce a synergistic disentangling activity when applied to hair.

* * * * *

UNITED STATES PATENT AND TRADEMARK OFFICE
CERTIFICATE OF CORRECTION

PATENT NO.: 5,612,025

DATED: March 18, 1997

INVENTOR(S): Daniele CAUWET-MARTIN et al.

It is certified that an error appears in the above-identified patent and that said Letters Patent is hereby corrected as shown below:

IN THE CLAIMS

Claim 1, column 11, line 38, insert --and-- after "acid,".

Claim 25, column 12, line 62, delete "contacing" and insert --contacting--.

Claim 26, column 13, line 15, insert --and-- after "acid,".

Claim 27, column 14, line 4, in the formula, delete "X" (both occurrences) and insert -- X$^-$--

Claim 27, column 14, line 13, insert --and-- after "acid,".

Signed and Sealed this

Fifteenth Day of July, 1997

Attest:

BRUCE LEHMAN

Attesting Officer

Commissioner of Patents and Trademarks